(12) United States Patent
Lei

(10) Patent No.: US 11,116,482 B2
(45) Date of Patent: *Sep. 14, 2021

(54) TEST BARREL

(71) Applicants: ZHEJIANG ORIENT GENE BIOTECH CO., LTD, Zhejiang (CN); HEALGEN SCIENTIFIC LIMITED, Houston, TX (US)

(72) Inventor: Siyu Lei, Anji (CN)

(73) Assignees: HEALGEN SCIENTIFIC LIMITED, Houston, TX (US); ZHEJIANG ORIENT GENE BIOTECH CO., LTD, Anji (CN)

( * ) Notice: Subject to any disclaimer, the term of this patent is extended or adjusted under 35 U.S.C. 154(b) by 115 days.

This patent is subject to a terminal disclaimer.

(21) Appl. No.: 15/475,891

(22) Filed: Mar. 31, 2017

(65) Prior Publication Data
US 2018/0103936 A1    Apr. 19, 2018

(30) Foreign Application Priority Data
Oct. 19, 2016  (CN) .......................... 201621134130.5

(51) Int. Cl.
*B01L 3/00* (2006.01)
*A61B 10/00* (2006.01)
(Continued)

(52) U.S. Cl.
CPC .......... *A61B 10/0096* (2013.01); *B01L 3/508* (2013.01); *B65D 1/00* (2013.01);
(Continued)

(58) Field of Classification Search
CPC ........ B01L 3/50; B01L 3/502; B01L 3/50825; B01L 2300/04; B01L 2300/041; G01N 21/01; G01N 33/00; B65D 41/0471
See application file for complete search history.

(56) References Cited

U.S. PATENT DOCUMENTS 4,955,645 A * 9/1990 Weems ................... F16B 7/182
                                                    285/355
6,277,646 B1 * 8/2001 Guirguis .............. A61B 10/007
                                                    422/417
(Continued)

*Primary Examiner* — Jill A Warden
*Assistant Examiner* — Dwayne K Handy
(74) *Attorney, Agent, or Firm* — NZ Carr Law Office

(57) ABSTRACT

Disclosed is a test barrel, to prevent a test liquid in the barrel from sputtering into a connection gap due to shaking of the barrel to hence cause contamination, improve the measurement accuracy in case of multiple tests, and meanwhile improve the operability of screwing on and screwing off the entire device during use of the device. The above technical objective of this utility model is implemented by employing the following technical solution: a test barrel, comprising barrel lid and a barrel body; wherein the threaded rings are arranged on an inner wall of a side face of the barrel lid and an outer wall of an opening of the barrel body, a rotary force applying portion is arranged on an outer wall of the side face of the barrel lid, and during engagement, a liquid blocking washer is arranged between the barrel lid and the barrel body, wherein a radial width of the liquid blocking washer is greater than a thickness of the opening of the barrel body.

8 Claims, 3 Drawing Sheets

(51) Int. Cl.
*B65D 43/02* (2006.01)
*B65D 1/00* (2006.01)
*B65D 41/04* (2006.01)

(52) U.S. Cl.
CPC ..... *B65D 41/0471* (2013.01); *B65D 43/0231* (2013.01); *B01L 2200/0689* (2013.01); *B01L 2200/087* (2013.01); *B01L 2200/141* (2013.01); *B01L 2300/042* (2013.01); *B01L 2300/0832* (2013.01); *B01L 2300/0848* (2013.01); *B65D 41/0442* (2013.01); *B65D 2543/00092* (2013.01); *B65D 2543/00537* (2013.01); *B65D 2555/02* (2013.01)

(56) References Cited

U.S. PATENT DOCUMENTS

| | | | |
|---|---|---|---|
| 6,342,183 B1 * | 1/2002 | Lappe | B01L 3/502 |
| | | | 422/417 |
| 10,656,138 B2 * | 5/2020 | Lei | B01L 3/502 |
| 2003/0022392 A1 * | 1/2003 | Hudak | B01L 3/502 |
| | | | 436/518 |
| 2005/0106750 A1 * | 5/2005 | Tung | A61B 10/007 |
| | | | 436/169 |
| 2012/0190122 A1 * | 7/2012 | Lin | A61B 10/0096 |
| | | | 436/161 |

* cited by examiner

TEST BARREL

CROSS-REFERENCE TO RELATED APPLICATIONS

This application claims the priority and benefit of Chinese Nat'l Patent App. Ser. No. 201621134130.5, filed Oct. 19, 2016.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO AN APPENDIX SUBMITTED ON A COMPACT DISC AND AN INCORPORATED BY REFERENCE OF THE MATERIAL ON THE COMPACT DISC

Not applicable.

STATEMENT REGARDING PRIOR DISCLOSURES BY THE INVENTOR OR A JOINT INVENTOR

Reserved for a later date, if necessary.

BACKGROUND OF THE INVENTION

Field of Invention

This utility model relates to the field of test, and in particular, relates to a test barrel.

Background of the Invention

In medical diagnosis field, body fluid testing is very common. Body fluid samples are tested by using devices having reagent strips to detect whether the analyzed substances are contained in the samples, which is described in many prior arts. These reagent strips generally comprise a reagent region and a test region, wherein the reagent region may comprise a sample receiving area and a marker area. The test region comprises an area displaying a test result and a test result comparison area in the downstream of the test region. Typically, the test result displaying area may be strip-shaped, and color changes are indicated in the test result displaying area to indicate whether the sample contains the analyzed substance. At present, the test paper cards available in the market are generally simple in design, and are inconveniently to secure, and therefore, a container for placing a test paper card is desired. Chinese patent application No. CN201610536307.2 has disclosed a test barrel for placing a test paper card. In the technical solution disclosed in this patent application, the test paper card may be secured to the test barrel. However, the test barrel has a lot of disadvantages in terms of structure. Firstly. The barrel lid and the barrel body is jointed with each other via engagement of the threads, and if the barrel shakes and causes the test liquid in the test barrel to sputter to the joint gap between the barrel lid and the barrel cover or inbetween the thread turns, the test barrel may be contaminated, which affects the accuracy of the subsequent test. Secondly, at the force bearing portion on the barrel lid, a side face on one side thereof which the finger is in contact with while screwing on the barrel lid is provided with bands, and the other side face is not provided with bands. This may result in poor operability during screwing-off.

SUMMARY OF THE INVENTION

This utility model is intended to provide a test barrel to prevent a test liquid in the barrel from sputtering into a connection gap due to shaking of the barrel to hence cause contamination, improve the measurement accuracy in case of multiple tests, and meanwhile improve the operability of screwing on and screwing off the entire device during use of the device.

The above technical objective of this utility model is implemented by employing the following technical solution: a test barrel, comprising barrel lid and a barrel body; wherein the threaded rings are arranged on an inner wall of a side face of the barrel lid and an outer wall of an opening of the barrel body, a screwing force applying portion is arranged on an outer wall of the side face of the barrel lid, and during engagement, a liquid blocking washer is arranged between the barrel lid and the barrel body, wherein a radial width of the liquid blocking washer is greater than a thickness of the opening of the barrel body.

The liquid blocking washer may be made from an elastic rubber or similar elastic material. During use, the liquid blocking washer is arranged on the opening of the barrel body, the barrel lid and the barrel body are engaged with each other, and the barrel lid, the liquid blocking washer and the barrel body are tightly engaged with each other. The screwing force applying portion on the outer wall of the side face of the barrel lid achieves an effect of bearing the force in case of both screw-on and screw-off. Since the radial width of the screwing force applying portion is greater than the thickness of the opening of the barrel body, the test liquid in the barrel would not, due to the vibration and shaking of the barrel body, sputter into the gap between the barrel lid and the barrel body. This prevents the case where a next test result or is affected due to incomplete or poor cleaning or the residual test liquid corrodes the test barrel, and improves the measurement accuracy in case of multiple tests. In addition, while achieving the effect of isolation, the liquid blocking washer may also reduce the friction between the barrel lid and the barrel body, mitigates damages therebetween, and prolongs the service life thereof.

As a preferred solution of this utility model, the barrel body is provided with a positioning portion, wherein the positioning portion is provided with a place reminding portion, and a mating portion is provided on the barrel lid, the mating portion being a hollow structure, and a contacting portion being provided within the hollow structure.

The shape and size of the positioning portion are the same or approximate to those of the mating portion. The place reminding portion may be a strip-shaped bump. The contacting portion is a strip-shaped elastic piece abutting against the place reminding portion in case of proper engagement, to prevent over-engagement of the barrel lid, and prevent damages caused due to over-press of the liquid blocking washer and the barrel body. When the barrel lid is screwing on for engagement, whether the barrel lid is properly screwed on may be judged by judging whether the mating portion is in coincidence with the positioning portion in terms of shape and position. Then, the applied force is reduced. When the place reminding portion is in contact with the contacting portion, a collision sound may be generated, which indicates that the screw-on is proper, and thus the proper screw-on may be visually identified.

As a preferred solution of this utility model, a securing mating portion is arranged between the opening of the barrel body and the liquid blocking washer.

The liquid blocking washer is arranged between the barrel lid and the barrel body. If the liquid blocking washer is positioned, the liquid blocking washer will rotate with the screw-on of the barrel lid, and during the rotation, bending press may be caused to a part of the liquid blocking washer. This may affect the sealing effect. The liquid blocking washer is secured to the barrel body, which prevents the above case.

As a preferred solution of this utility model, the securing mating portion comprises projecting granules on an edge of the opening of the barrel body and a concave opening on the liquid blocking washer.

The liquid blocking washer is sleeved onto the projecting granules via the concave opening and positioned on the barrel body, which is simple and convenient, and improves the operability in securing.

As a preferred solution of this utility model, the projecting granules are arranged on an outer side of the edge of the opening of the barrel body, and the concave opening is arranged on a side of an outer ring wall of the of the liquid blocking ring.

The projecting granules are arranged on or proximal to the outer side of the edge of the opening of the barrel body, the concave opening is arranged on or proximal to the side of the outer ring wall of the liquid blocking ring to prevent the case where the test liquid in the barrel from sputtering into the securing mating portion. The projecting granules and the concave opening are arranged on the outer side to prevent the above case.

As a preferred solution of this utility model, the barrel body is of a cylindrical shape, and an anti-slip gripping portion is arranged on an outer wall of the barrel body, and a securing rib for securing a test paper card is arranged on an inner wall of the barrel body.

The barrel body is of a cylindrical shape instead of a cuboid shape, which is more favorable for gripping thereof in the palm or purlicue. In addition, in the case where the amount of the test liquid contained remains unchanged, fewer materials are desired. The test barrel contains a test liquid and a test paper card. The test paper card may be secured by the securing ribs. If the barrel wall is not subjected to any anti-slip treatment, the barrel is apt to slip off from the hands during griping, and as a result the test barrel may shake or even drop off. This is unfavorable to the test accuracy, and shortens the service life of the test barrel.

As a preferred solution of this utility model, the anti-slip gripping portion is formed by oblique bands arranged on an outer wall of the barrel body.

Oblique bands are parallelly arranged on the outer wall face of the barrel body. Since the winkles are oblique, these bands may prevent both transversal and longitudinal drop-offs.

As a preferred solution of this utility model, a liquid flowing face is arranged on an inner side of the barrel lid.

Considering that the test liquid would sputter to the contacting portion between the liquid blocking washer and the barrel lid, the liquid flowing portion may lead flowing of the test liquid attached on the surface of the gap, such that the test liquid more easily drops off.

As a preferred solution of this utility model, the liquid flowing face is a circular arc surface smoothly tangent to an inner lid surface of the barrel lid. In conclusion, this utility model has the following beneficial effects:

1. The screwing force applying portion on the outer wall of the side face of the barrel lid achieves an effect of bearing the force in case of both screw-on and screw-off. In addition, while achieving the effect of isolation and improving the measurement accuracy in case of multiple tests, the liquid blocking washer may also reduce the friction between the barrel lid and the barrel body, mitigates damages therebetween, and prolongs the service life thereof.

2. The place reminding portion and the contacting portion may prevent over-engagement of the barrel lid, and prevent damages caused due to over-press of the liquid blocking washer and the barrel body. Whether the barrel lid is properly screwed on may be judged by judging whether the mating portion is in coincidence with the positioning portion in terms of shape and position, such that the proper screw-on may be visually identified.

3. The barrel body is of a cylindrical shape instead of a cuboid shape, which is more favorable for gripping thereof in the palm or purlicue; and the oblique bands parallelly arranged on the outer wall of the barrel body may prevent transversal and longitudinal drop-offs.

4. The liquid flowing portion may lead flowing of the test liquid attached on the surface of the gap, such that the test liquid more easily drops off.

BRIEF DESCRIPTION OF THE SEVERAL VIEWS OF THE DRAWINGS

Other objectives of the disclosure will become apparent to those skilled in the art once the invention has been shown and described. The manner in which these objectives and other desirable characteristics can be obtained is explained in the following description and attached figures in which.

Figure 1:
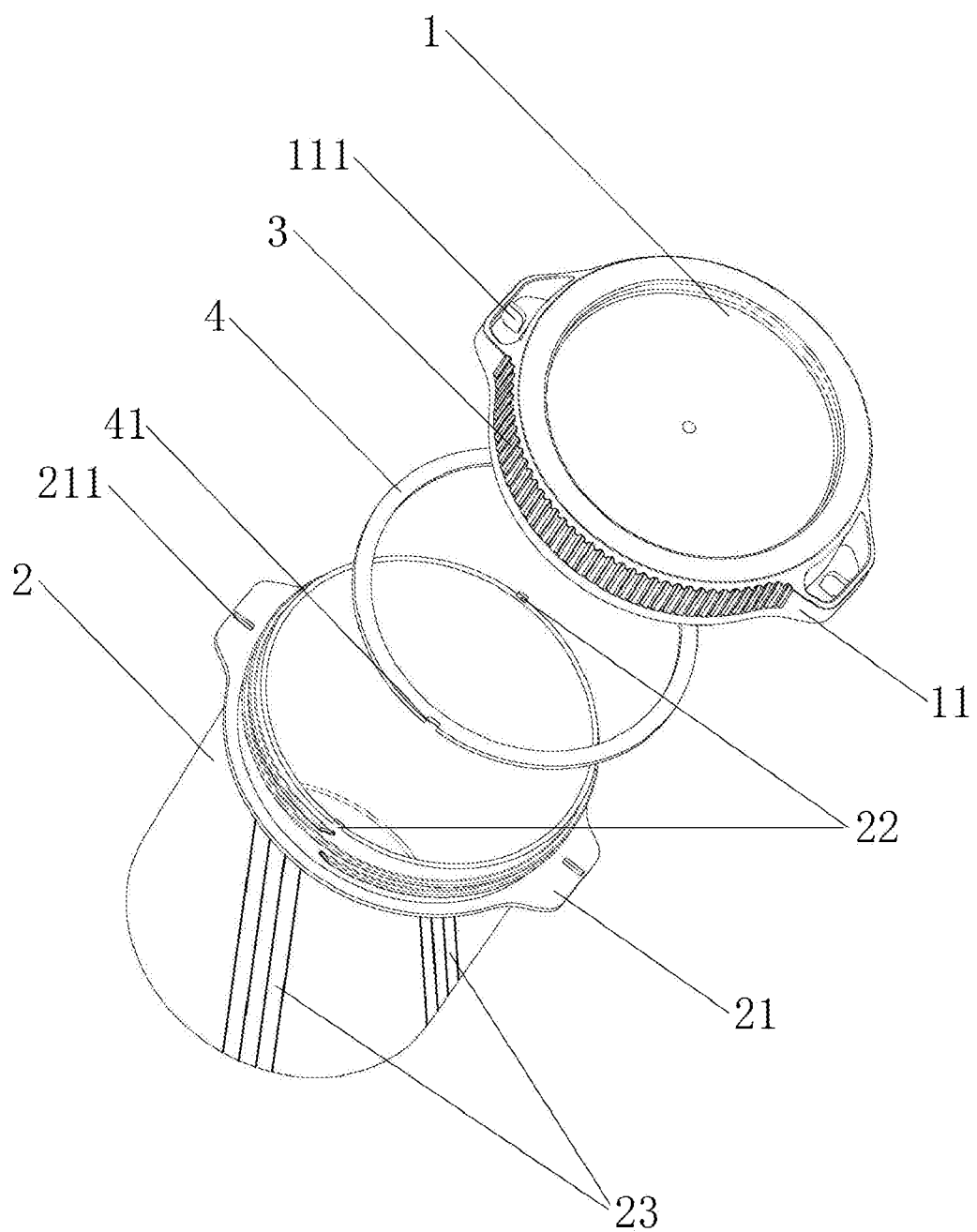
FIG. 1 is a schematic structural view of a test barrel.

In the drawings, 1 denotes a barrel lid, 11 denotes a mating portion, 111 denotes a contacting portion, 12 denotes a liquid flowing face, 13 denotes an inner lid face of the barrel lid, 2 denotes a barrel body, 21 denotes a positioning portion, 211 denotes a place reminding portion, 22 denotes a projecting granule, 23 denotes an anti-slip griping portion, 24 denotes a securing rib, 3 denotes a screwing force applying portion, 4 denotes a liquid blocking washer, and 41 denotes concave opening.

It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFERRED EMBODIMENTS

This utility model is further described with reference to the accompanying drawings.

The specific embodiments herein are merely intended to interpret this utility model, instead of limiting the present invention. Upon reading the specification herein, a person skilled in the art would make modifications of no innovative contributions to the embodiments, and these modifications shall be protected by the patent right as long as they fall within the scope defined by the claims of this utility model.

Embodiment 1: FIG. 1 is a schematic structural view of a test barrel. The test barrel comprises a barrel lid 1 and a barrel body 2; wherein the threaded rings are arranged on an inner wall of a side face of the barrel lid 1 and an outer wall of an opening of the barrel body 2, a screwing force applying portion 3 is arranged on an outer wall of the side face of the barrel lid 1.

Figure 2:
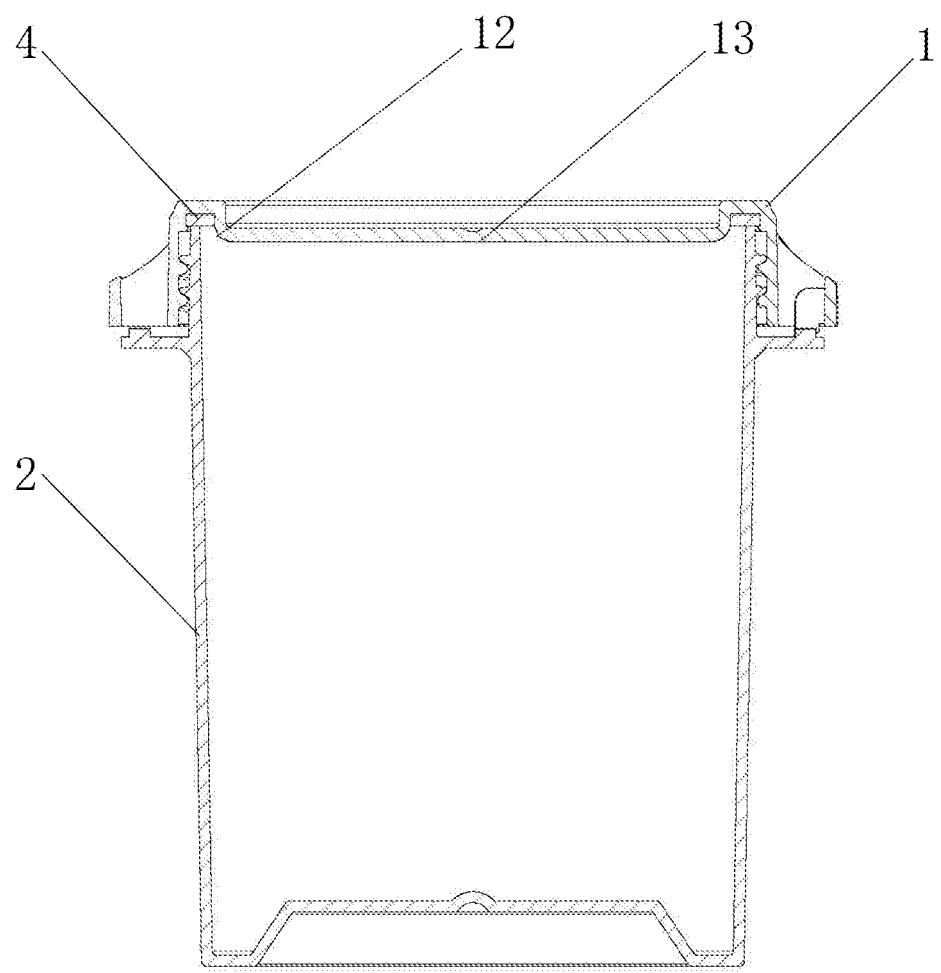
FIG. 2 is a sectional view when a test barrel is tightly whirled.

As illustrated in FIG. 2, during engagement, a liquid blocking washer 4 is arranged between the barrel lid 1 and the barrel body 2, wherein a radial width of the liquid blocking washer 4 is greater than a thickness of the opening of the barrel body 2.

Figure 3:
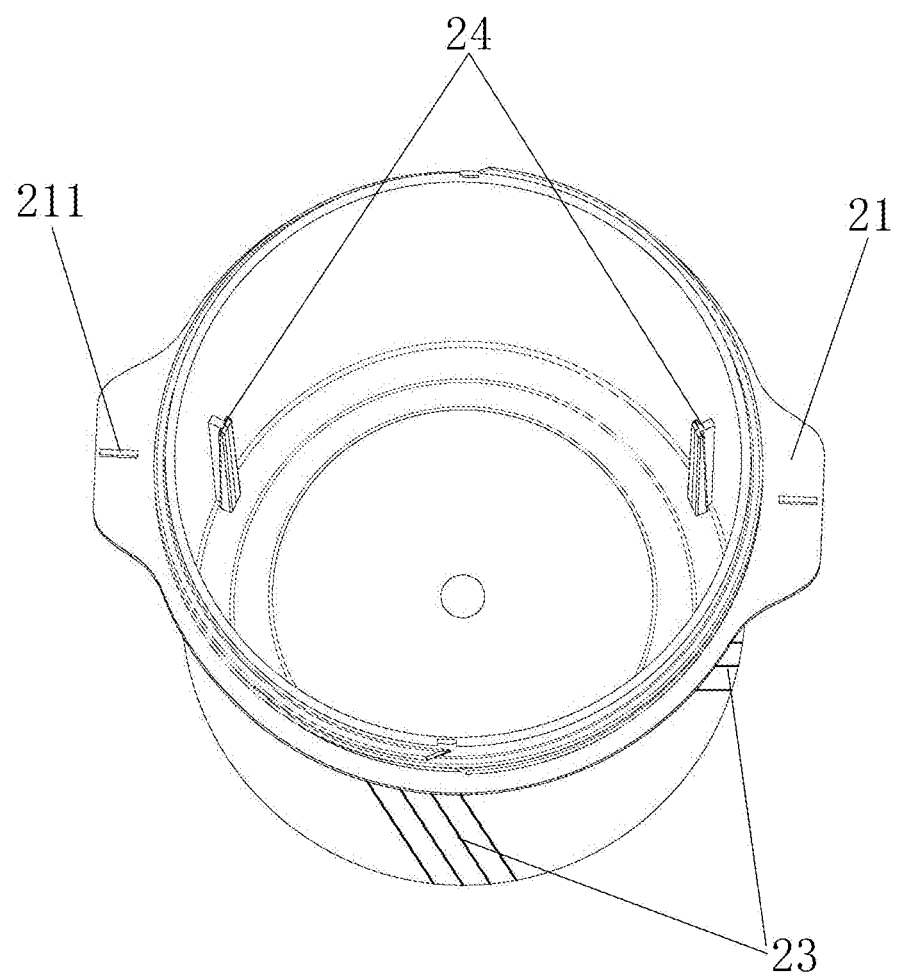
FIG. 3 is a schematic view of a barrel body.

As illustrated in FIG. 1 and FIG. 3, the barrel body (2) is provided with a positioning portion 21, wherein the positioning portion 21 is provided with a place reminding portion 211, and a mating portion 11 is provided on the barrel lid 1, the mating portion 11 being a hollow structure, and a contacting portion 111) being provided within the hollow structure. The shape and size of the positioning portion 21 are the same as or approximate to those of the mating portion 11. A securing mating portion is arranged between the opening of the barrel body 2 and the liquid blocking washer 4. The securing mating portion comprises projecting granules 22 on an edge of the opening of the barrel body 2 and a concave opening 41 on the liquid blocking washer 4. The projecting granules 22 are arranged on or proximal to an outer side of the edge of the opening of the barrel body 2, and the concave opening 41 is arranged on or proximal to a side of an outer ring wall of the of the liquid blocking ring 4. The barrel body 2 is of a cylindrical shape, and an anti-slip gripping portion 23 is arranged on an outer wall of the barrel body 2, and a securing rib 24 for securing a test paper card is arranged on an inner wall of the barrel body 2. The anti-slip gripping portion 23 is formed by oblique bands arranged on an outer wall of the barrel body 2, to prevent transversal and longitudinal drop-offs.

As illustrated in FIG. 2, a liquid flowing face 12 is arranged on an inner side of the barrel lid 1. The liquid flowing face 12 is a circular arc surface smoothly tangent to an inner lid surface 13 of the barrel lid.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus the breadth and scope of the claimed invention should not be limited by any of the above-described embodiments.

Terms and phrases used in this document, and variations thereof, unless otherwise expressly stated, should be construed as open-ended as opposed to limiting.

As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

All original claims submitted with this specification are incorporated by reference in their entirety as if fully set forth herein.

What is claimed is:

1. A test barrel, characterized by comprising:
    a barrel lid (1) having a face and the face having an inner wall, and
    a barrel body (2) having an opening and an outer wall near to the opening, wherein the inner wall having threaded rings and wherein the outer wall of the barrel body having threaded rings, a rotary force applying portion (3) is arranged on an outer wall of the side face of the barrel lid (1), and during engagement, a liquid blocking washer (4) is arranged between the barrel lid (1) and the barrel body (2), wherein a radial width of the liquid blocking washer (4) is greater than a thickness of the opening of the barrel body (2),
    wherein the barrel body (2) is provided two positioning portions (21) and each of the positioning portions is provided with one place reminding portion (211) that has one strip-shaped bump thereon,
    wherein two mating portions (11) are provided on the barrel lid (1), and each of the mating portions having one hollow structure and one contacting portion (111) is provided within the hollow structure, and wherein the contacting portion (111) is one strip-shaped elastic piece for abutting against the strip-shaped bump, and
    when the strip-shaped elastic piece is in contact with the strip-shaped bump, a collision sound is generated by the strip-shaped elastic piece as to indicate if the barrel lid is properly screwed on the barely body and to prevent over-engagement of the barrel lid, and prevent damages caused due to over-press of the liquid blocking washer and the barrel body, and
    wherein the shape and size of the position portion (21) are the same to those of the mating portion (11) and when the barrel lid is screwing on for engagement with the barrel body, whether the barrel lid is properly screwed on the barrel body is further to be judged by judging whether the mating portion is in coincidence with the positioning portion in terms of shape and position.

2. The test barrel according to claim 1, characterized in that: a securing mating portion is arranged between the opening of the barrel body (2) and the liquid blocking washer (4).

3. The test barrel according to claim 2, characterized in that: the securing mating portion comprises projecting granules (22) on an edge of the opening of the barrel body (2) and a concave opening (41) on the liquid blocking washer (4).

4. The test barrel according to claim 3, characterized in that: the projecting granules (22) are arranged on an outer side of the edge of the opening of the barrel body (2), and the concave opening (41) is arranged on a side of an outer ring wall of the liquid blocking ring (4).

5. The test barrel according to claim 1, characterized in that: the barrel body (2) is of a cylindrical shape, and an anti-slip gripping portion (23) is arranged on an outer wall of the barrel body (2), and a securing rib (24) for securing a test paper card is arranged on an inner wall of the barrel body (2).

6. The test barrel according to claim 5, characterized in that: the anti-slip gripping portion (23) is an oblique wrinkle arranged on an outer wall of the barrel body (2).

7. The test barrel according to claim 1, characterized in that: a liquid flowing face (12) is arranged on an inner side of the barrel lid (1).

8. The test barrel according to claim 1, characterized in that: the liquid flowing face (12) is a circular arc surface smoothly tangent to an inner lid surface (13) of the barrel lid.

* * * * *